(12) United States Patent
Choy et al.

(10) Patent No.: US 6,708,693 B1
(45) Date of Patent: Mar. 23, 2004

(54) METHOD AND DEVICE FOR POSITIONING A PATIENT FOR THE DIAGNOSIS OF HERNIATED LUMBAR DISC DISEASE

(76) Inventors: Daniel S-J Choy, 300 E. 74th St., New York, NY (US) 10021; Arpad Fejos, Jr., 720 W. 170th St., (Apt. 2-I), New York, NY (US) 10032; Arpad Fejos, Sr., 211 Riverview Dr., Dryden, Ont. (CA), P8N 1W6

( * ) Notice: Subject to any disclaimer, the term of this patent is extended or adjusted under 35 U.S.C. 154(b) by 0 days.

(21) Appl. No.: 10/103,227

(22) Filed: Mar. 21, 2002

(51) Int. Cl.[7] ................................................ A61G 15/00
(52) U.S. Cl. ......................... 128/845; 602/32; 128/875
(58) Field of Search ................................ 128/846, 869, 128/870, 874, 875; 602/19, 32–40

(56) References Cited

U.S. PATENT DOCUMENTS

| | | | |
|---|---|---|---|
| 2,660,999 A | * | 12/1953 | Thornton |
| 2,822,805 A | * | 2/1958 | Hill |
| RE30,501 E | * | 2/1981 | Almeida ..................... 128/80 C |
| 4,483,330 A | * | 11/1984 | Jacobsen ...................... 128/75 |
| 4,641,637 A | * | 2/1987 | Rosen ........................... 128/75 |
| 4,674,483 A | * | 6/1987 | Frederick ..................... 128/75 |
| 4,799,497 A | | 1/1989 | Riley, II |
| 5,875,781 A | * | 3/1999 | Klaus ......................... 128/869 |
| 6,000,399 A | | 12/1999 | Choy |

* cited by examiner

*Primary Examiner*—Michael A. Brown
(74) *Attorney, Agent, or Firm*—Schweitzer Cornman Gross & Bondell LLP

(57) ABSTRACT

A method and device for selectively creating intra-spinal pressure in a patient allows improved diagnosis of spinal disorders, particularly through MRI imaging. A harness is worn by the patient above the spinal area to be imaged and the patient lies supine. The harness is connected to a tensioning unit located at the feet of the patient. Tension is applied to the harness through a pair of straps while the patient's feet rest against a stop or plate and the patient's legs are locked. The applied tension compresses and flexes the spine to initiate the condition to be diagnosed. The patient can then be repositioned for imaging while the tension is applied. An indicator may be employed to allow the applied force to be monitored.

11 Claims, 4 Drawing Sheets

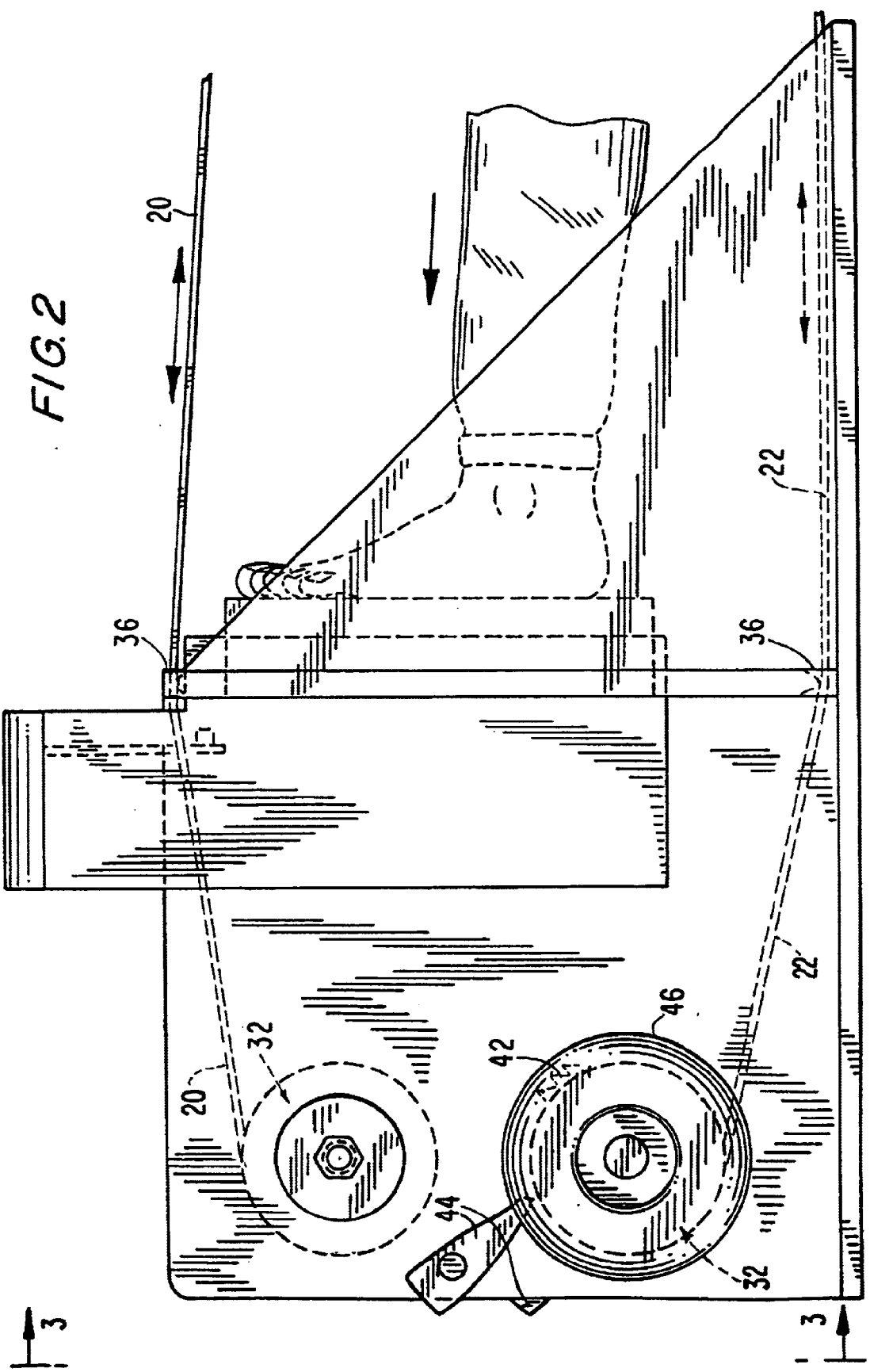

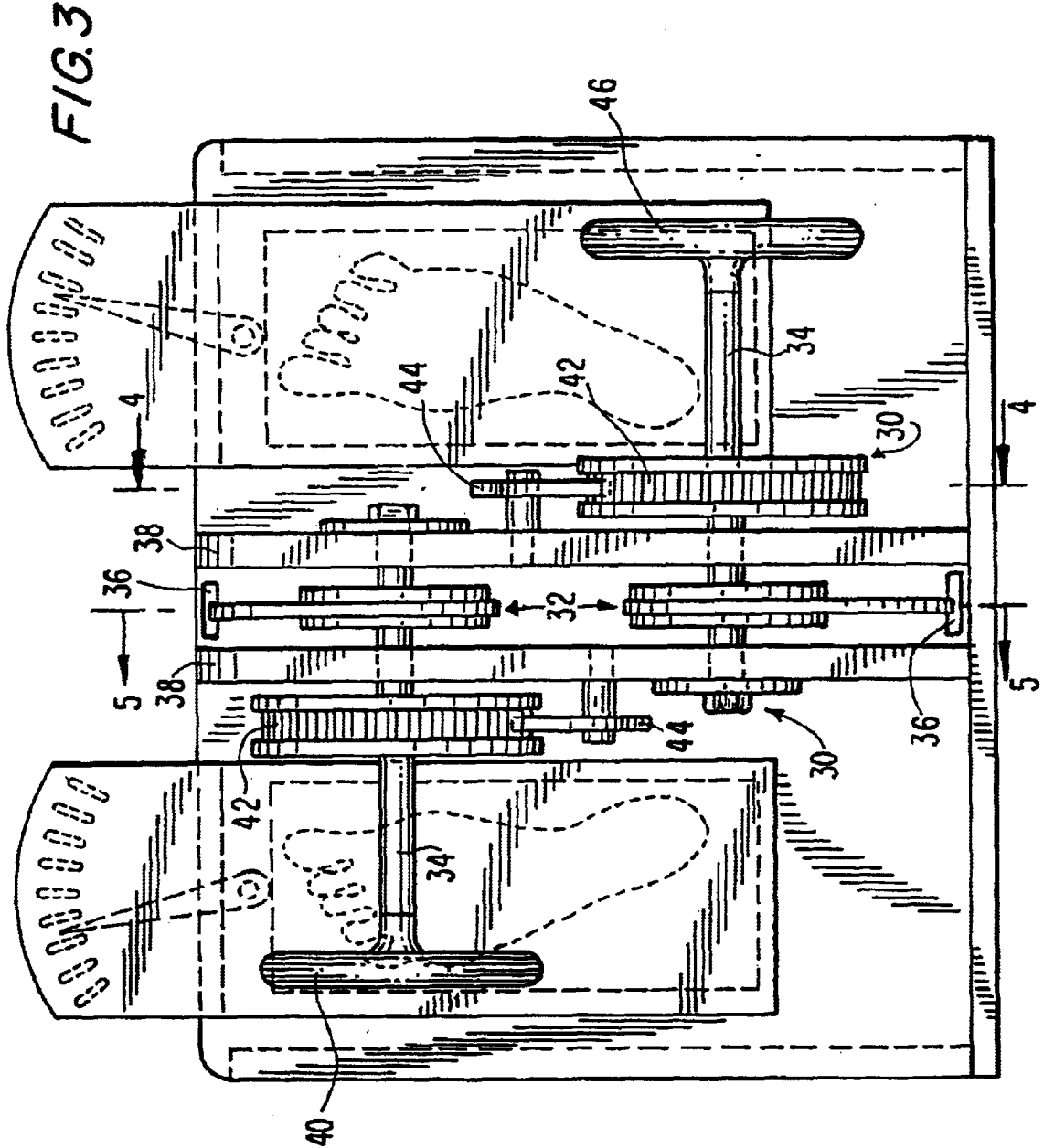

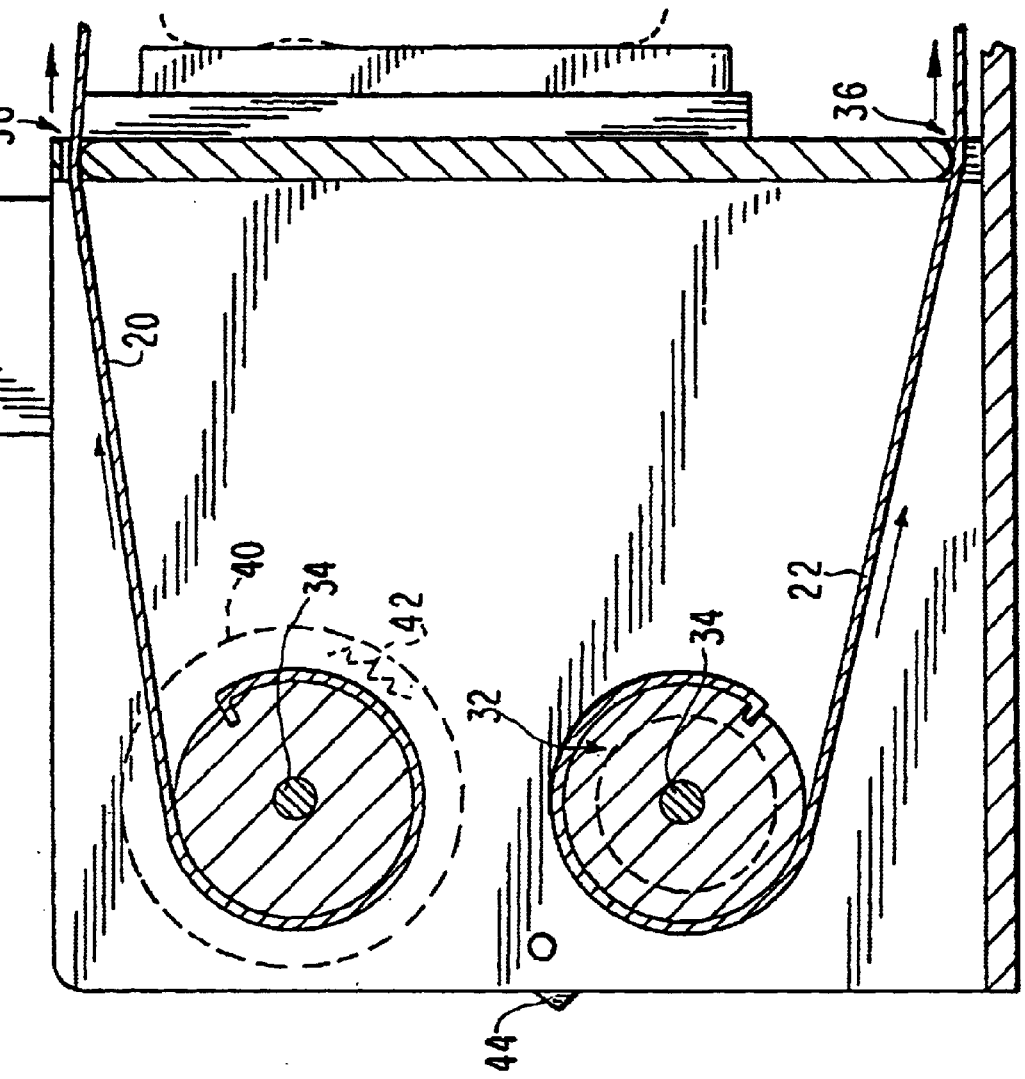
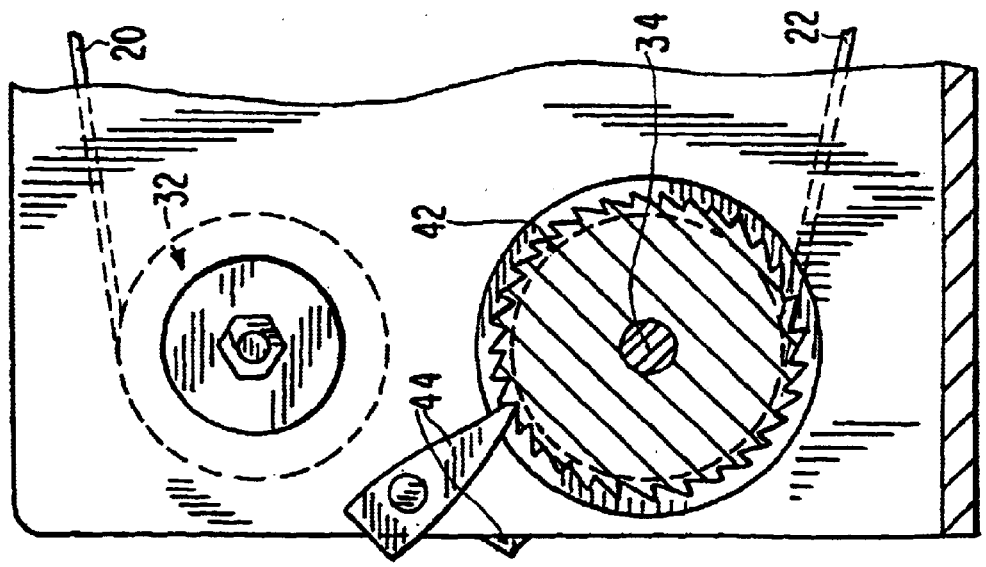

METHOD AND DEVICE FOR POSITIONING A PATIENT FOR THE DIAGNOSIS OF HERNIATED LUMBAR DISC DISEASE

The present invention relates to a new and improved method and device to be used in conjunction with the diagnosis of herniated lumbar disc disease, particularly in humans.

BACKGROUND OF THE INVENTION

The human spinal or vertebral column consists of a plurality of separate vertebrae, joined to each other to permit forward, backward and sideways movement of the column. At the lower end of the spinal column are the lumbar vertebrae which support the small of the back. Above the lumbar vertebrae are the thoracic vertebrae, which lie behind the thoracic or chest cavity. The uppermost cervical vertebrae define the skeletal framework of the neck. The vertebrae are separated and supported against each other by cushioning elements or discs, and are held together by ligaments. The discs are subject to deterioration and deformation, often creating significant pain.

Studies have shown that the intra-disc pressure in the lumbar spine while in a supine position is in the neighborhood of 15–25 Kpa, while pressures while in a sitting position average between 150 and 200 Kpa. These correspond roughly to pressures of 7.5 and 30 psi, respectively. The observation that patients with herniated lumbar disc disease are least comfortable in a sitting position may be at least partially due to such pressure differences.

Magnetic Resonance Imaging (MRI) techniques are often used in the diagnosis of lumbar disc disease. Experience has shown, however, that it is not uncommon to find a disassociation between the severity of a patient's clinical symptoms and evidence of disease shown through MRI findings. The disassociation can be in part explained by the general inability of conventional MRI diagnosis systems to allow the patient to be imaged when placed into a variety of positions, including the sitting position, to vary the intra-discal pressures and alignment of the vertebrae. The supine position, in which all conventional MRIs of the lumbosacral spine are performed, is associated with the lowest intra-discal pressure, and is thus not a good position to provoke disc herniation, and is thus far from an optimal position for effective disc herniation diagnosis. It has been shown, for example, than an L5-S1 protrusion was noticeably augmented when the patient was in the sitting position.

In U.S. Pat. Nos. 6,000,399 and 5,762,073 to one of the present inventors, a method and apparatus for positioning a patient more optimally for lumbar disc disease MRI diagnosis is set forth. Such a method and apparatus requires the patient, while lying in a supine position, to be positioned between first and second force-accepting means at opposed ends of a frame with the patient's knees slightly bent. With the patient applying muscular force to straighten the knees, and the patient's body restrained by the force-accepting means, compression is placed on the lumbar spine. MRI imaging conducted during the force exertion allows the herniation provoked by be compression to be identified and observed.

While the aforementioned method and apparatus significantly improve the accuracy and efficiency of MRI lumbar disc disease diagnosis, such methodology and device is subject to several shortcomings. The patient may be unable to exert sufficient force for a sufficient length of time to allow a proper MRI image to be created. Alternatively, the patient, while physically able to generate sufficient pressure, may be under significant pain when such pressure is applied to prevent maintenance of the pressure. Further, while force generated by the patient can be monitored, it is often difficult to direct the patient to exert a particular amount of force to assist in associating the level of force with the degree of herniation.

It is accordingly the purpose of the present invention to provide an improved method and device for positioning a patient for the diagnosis of herniated lumbar disc disease in connection with MRI diagnosis procedures.

A further purpose of the present invention is to provide such a method and device which does not require the active participation by the patient.

Still a further purpose of the present invention is to provide such a method and device which can allow the force applied to the patient to be varied incrementally and to be continuously monitored during the application thereof.

BRIEF DESCRIPTION OF THE INVENTION

In accordance with the foregoing and other objects and purposes, a device constructed in accordance with the present invention comprises a harness that engages the patient while lying in a supine position at a location above the lumbar spine area and a footrest against which the patient's feet are placed. The harness is connected to a tensioning device located at the footrest. The patient lies with his or her feet against the footrest of the device and with the knees in a locked position. In accordance with the invention's methodology, a tensioning force is applied to the harness, which is transmitted to the patient and compresses the spine, and particularly the lumbar portion thereof. With the tension and compression applied, the patient is positioned within the MRI imaging apparatus and an image is taken. The amount of compression is adjustable; indicators may be provided to provide a constant readout of the tension and thus pressure applied to the spine.

BRIEF DESCRIPTION OF THE DRAWINGS

A fuller understanding of the present invention will be accomplished upon consideration of the following detailed description of a preferred, but nonetheless illustrative embodiment of the invention, when considered in association with the annexed drawings, wherein:

FIG. 2 is an elevation view taken along line 2—2 of FIG. 1;

FIG. 3 is an end elevation view taken along line 3—3 in FIG. 2;

FIG. 4 is a section view taken along line 4—4 of FIG. 3; and

FIG. 5 is a section view taken along line 5—5 of FIG. 3.

DETAILED DESCRIPTION OF THE INVENTION

Figure 1:
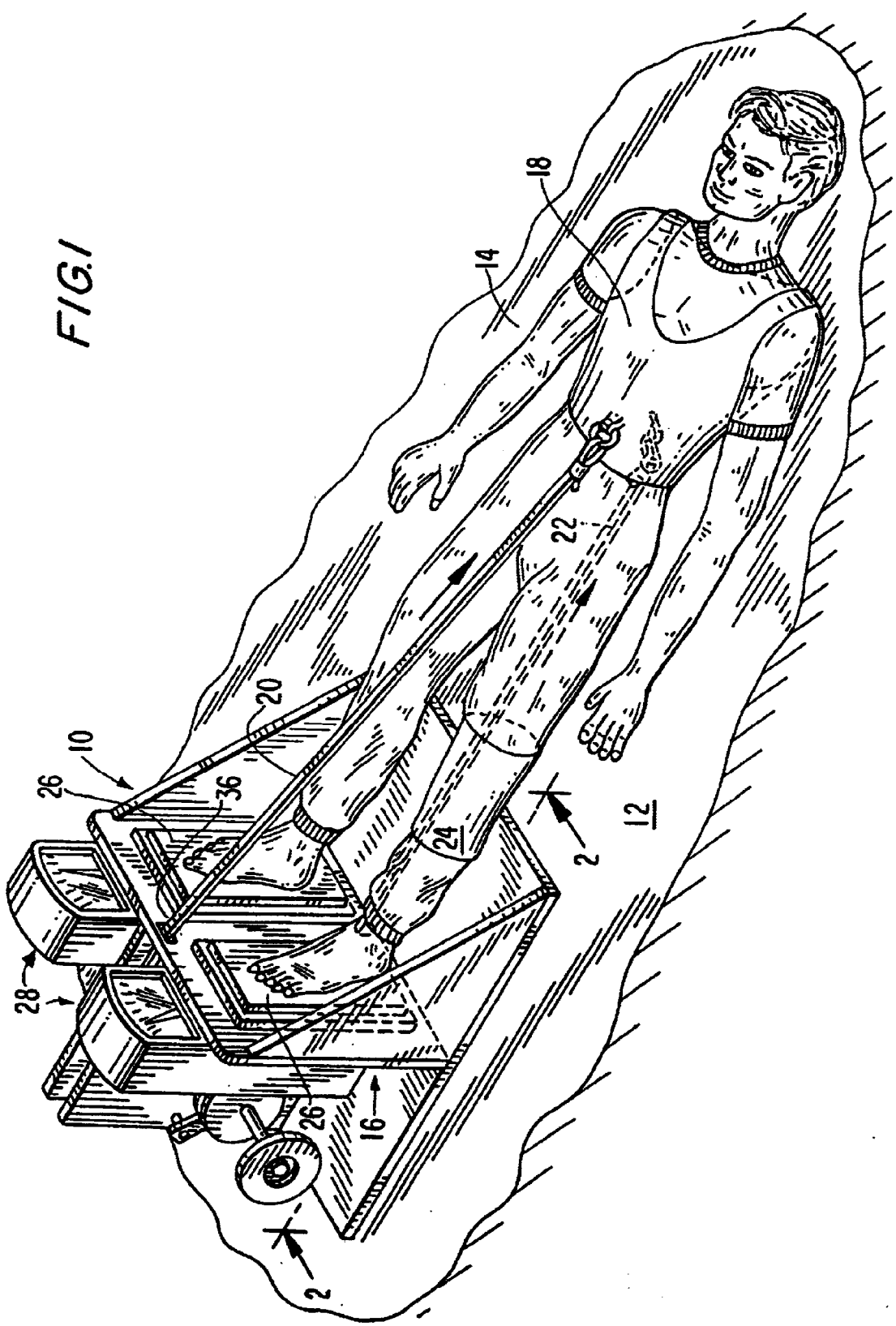
FIG. 1 is a perspective view of the invention.

Referring initially to FIG. 1, the present invention 10 is intended to be installed upon an MRI diagnosis platform 12 to place a patient 14 in spinal compression such that the platform 12, when positioned within an MRI imaging zone, allows an MRI image to be taken of the patient in spinal compression and flexion. As may be seen, the patient lies supine upon the platform 12 with his or her legs extended and feet in contact with the footrest/restraining board 16 of the apparatus. The patient wears a harness 18, positioned above the spinal area to be compressed and imaged. A tensioning system of the apparatus tensions a pair of straps 20, 22 affixed to the harness, pulling the harness towards the force restraining board 16, and thus compressing and flexing the patient's spine as required. The patient may be provided with a pair of knee braces 24 (only one of which is shown) to maintain the knees in the locked position to allow the pressure on the spine to be maintained and not relieved by knee flexion.

Preferably, each of the patient's feet are positioned on a footplate 26, with the force exerted by the foot against the footplate being indicated by indicator means 28. The indicator means is preferably a simple spring scale device. As depicted, each foot may be placed on a separate footplate. A single footplate can be used, however, with a single indicator means, to reduce cost. Each of the force-registering systems is. coupled to an associated indicator 28, which registers the force exerted by the respective foot which in turn is indicative of the compressive force applied to the patient through the harness 18 and thus applied to the spine.

The tensioning force is applied through the straps 20, 22 and harness 18 by a pair of tensioning units 30, each of which is associated with one of the straps. As further depicted in FIG. 3, each of the tensioning units 30 may include a take-up spool or core 32 mounted on a shaft 34 to which the end of a respective strap is affixed. The shafts 34 are journaled for rotation in spaced vertical plates 38 which extend rearwardly from the footrest 16. The straps 20, 22 pass through apertures 36 in the footrest main plate. Each shaft 34 further supports a hand wheel 40, as well as a gear 42 and associated pawl 44 which, as the shaft and take-up spool 32 is rotated to apply tension to the respective strap, provides a "one-way" action, maintaining the applied tension and preventing the tension in the straps from being inadvertently released. Appropriate means (not shown) for disengaging the pawl from the gear may be provided to allow tension to be released when the diagnostic procedure is completed. As may be appreciated, the manual tensioning system depicted may be replaced by other tensioning means, both manual or motorized. Use of a manually-operated system may be preferred, however, as it may facilitate the inclusion of non-metallic/non-ferrous components, the use of which may be important when the apparatus is used in MRI imaging environments which generate intense magnetic fields.

The use of a pair of tensioning units, allowing the tension in each of the straps to be adjusted independently, facilitates the application of tension to the harness and thus compression to the patient in a manner in which the resultant thereof is oriented directly through and co-linearly with the spine, thus assisting in maintaining the patient in the supine position with the spine slightly flexed, and without twisting which may occur if a single force-applying system is utilized.

In operation, the patient dons the harness and lies in a supine position with his or her feet against the footrests. The supporting straps 20, 22 are connected to the harness and the tension devices engaged. Tension is applied to the harness to the point where the compression applied to the patient, as indicated by the forces displayed on the indicators 28, corresponds to the appropriate compressive force level in the spine appropriate for herniation to be prominent. The patient is instructed to maintain his or her legs in the extended and locked position, as augmented and assisted by the knee braces 24, to maintain the applied tension. In general, the patient is also instructed to relax, maintaining an equal pressure against the footpads, without favoring either of the legs.

When the appropriate force level is reached and maintained, the examination platform 12 is positioned within the MRI imaging apparatus as appropriate to allow imaging of the spinal area to be performed. After imaging the platform is returned to a designated position and the tension upon the straps relieved. The harness is uncoupled from the straps and then removed from the patient.

We claim:

1. A device for the selective creation and maintenance of intra-spinal pressure in a patient during a diagnostic procedure in which the patient lies in a supine position, comprising:

a base having an upstanding plate against which the feet of the patient are placed;

a harness worn by the patient at a location above the portion of the patent's spine to be subject to the diagnostic procedure; and means coupled to the harness for applying a foot-directed force to the patient through the harness to compress and flex the patient's spine in a controlled manner and increase the intra-spinal pressure to a chosen level to permit the diagnostic procedure to be performed with the spine in a compressed state, said means comprising first and second straps respectively located anteriorly and posteriorly of the patient and means for independently varying tension in each of the straps.

2. The device of claim 1 further including indicator means for displaying the force applied to the patient.

3. The device of claim 2 wherein the upstanding plate supports at least one footplate against which the feet to the patient are placed, the indicator means comprising an indicator associated with the at least one footplate to display the force exerted by the feet against the at least one footplate.

4. The device of claim 1 further comprising means for maintaining the knees of the patient in a locked position as the foot-directed force is applied.

5. The device of claim 4 wherein the means for maintaining the knees of the patient in a locked position is a knee brace.

6. A method for creating and maintaining a chosen level of intra-spinal pressure in a patient while the patient is undergoing a diagnostic procedure, comprising the steps of affixing a harness to the patient above the portion of the patient's spine to be diagnosed;

having the patient lie in a supine position with the patient's feet against a stop;

applying a foot-directed force to the harness to compress and flex the patient's spine and increase intra-spinal pressure to the chosen level.

7. The method of claim 6 further including the step of connecting the harness to force-applying means located at the feet of the patient.

8. The method of claim 7 wherein the step of connecting the harness to force-applying means is carried out by connecting a pair of straps between the harness and force-applying means.

9. The method of claim 8 wherein the step of connecting the harness to force-applying means is carried out by connecting a first strap anteriorly of the patient and a second strap posteriorly of the patient.

10. The method of claim 6 further including the step of displaying the foot-directed force on an indicator.

11. The method of claim 6 further including the step of maintaining the patient's knees in a locked position as the foot-directed force is applied to the harness.

* * * * *